United States Patent [19]

Kashmer et al.

[11] Patent Number: 4,465,485
[45] Date of Patent: Aug. 14, 1984

[54] SUCTION CANISTER WITH UNITARY SHUT-OFF VALVE AND FILTER FEATURES

[75] Inventors: James S. Kashmer, Budd Lake; John K. Klimbach, Wayne; Randall P. Vendetti, Lincoln Park, all of N.J.

[73] Assignee: Becton, Dickinson and Company, Paramus, N.J.

[21] Appl. No.: 494,745

[22] Filed: May 16, 1983

Related U.S. Application Data

[63] Continuation of Ser. No. 241,153, Mar. 6, 1981, abandoned.

[51] Int. Cl.³ .............................................. A61M 1/00
[52] U.S. Cl. ....................................... 604/320; 55/215
[58] Field of Search .............................. 604/317–320, 604/322; 137/199, 205; 128/276–278, 760, 766, 200.25, 202.22, 205.27, 205.29, 206.17, 910; 55/279, 215, 528, 501, 503

[56] References Cited

U.S. PATENT DOCUMENTS

| 2,980,204 | 4/1961 | Jordan | 55/501 |
|---|---|---|---|
| 3,719,197 | 3/1973 | Pannier et al. | 128/276 |
| 3,738,381 | 6/1973 | Holbrook | 137/199 |
| 3,768,478 | 10/1973 | Fertik et al. | 604/320 |
| 3,782,083 | 1/1974 | Rosenberg | 128/205.29 |
| 4,013,076 | 3/1977 | Puderbaugh et al. | 128/276 |
| 4,111,204 | 9/1978 | Hessel | 128/276 |
| 4,187,390 | 2/1980 | Gore | 174/102 R |
| 4,228,798 | 10/1980 | Deaton | 128/276 |
| 4,275,732 | 6/1981 | Gereg | 128/276 |
| 4,346,711 | 8/1982 | Agdanowski et al. | 604/319 |

OTHER PUBLICATIONS

Gore-Tex. Expanded PTFE, W. L. Gore and Assoc. Inc., Elkton, Md., 1975, 1978.
Gore-Tex Membran Products, W. L. Gore & Assoc., Inc. Elkton, Md., 1980.

Primary Examiner—C. Fred Rosenbaum
Assistant Examiner—J. L. Kruter
Attorney, Agent, or Firm—Richard J. Rodrick; John L. Voellmicke

[57] ABSTRACT

A suction canister assembly comprises an enclosed receptacle having a first opening for providing suction to the receptacle and a second opening for drawing fluids, including liquids and gases, into the receptacle during suction. A unitary shut-off valve/filter element is associated with the interior side of the first opening. This element is oriented within the receptacle so as to be contacted by liquid in the receptacle which rises therein. The element is porous and is adapted to filter particulate matter from gas passing therethrough. In addition, the valve/filter element is capable of developing sufficiently high surface tension under liquid contact to serve as a barrier against liquid passage therethrough at pressure differentials across the element when vacuum is applied on one side of the element. As a result, the element is adapted to terminate suction through the suction opening when liquid rises in the receptacle to completely cover the element.

27 Claims, 7 Drawing Figures

SUCTION CANISTER WITH UNITARY SHUT-OFF VALVE AND FILTER FEATURES

This is a continuation of application Ser. No. 241,153, filed Mar. 6, 1981, now abandoned.

BACKGROUND OF THE INVENTION

1. Field of the Invention

The present invention relates to a suction canister, and more particularly, concerns a suction canister used for withdrawing and collecting body fluids from a patient during surgical procedures.

2. Description of the Prior Art

Suction canisters are employed in the hospital environment, and particularly during surgical procedures, to drain body liquids from a patient. In general, suction canisters employ a collection system and a vacuum source, such as a pump, to facilitate this drainage procedure. The canister generally includes a flexible line or hose connected to the vacuum source so that vacuum can be applied to the interior of the canister. Another flexible line or hose extends from the canister to the source of body liquids in the patient. Once the vacuum is applied, a negative pressure gradient is communicated through the interior of the suction canister so that body liquids are drawn into the canister.

As the suction canister fills, a need for controlling overflow has been recognized. To this end, a number of prior suction canister devices have employed shut-off valves to control any overflow of liquid from the canister. More particularly, previous devices have employed hydrophobic filters to prevent the passage of liquid out of the suction cansiter during operation. U.S. Pat. Nos. 3,719,197; 3,738,381; 4,013,076; 4,111,204 and patent application Ser. No.133,242, filed Mar. 24, 1980, the particulars of which the Applicant herein is familiar, disclose suction canisters wherein the use of hydrophobic material is employed for liquid control purposes. Both U.S. Pat. No. 4,111,204 and the abovementioned patent application use a hydrophobic material in conjunction with a filter bag disposed inside the suction canister.

In addition to the control of liquid overflow, suction canister systems have also been concerned with particulate matter control, including bacteria. U.S. Pat. No. 4,228,798, discloses a medical suction system with a hygroscopic filter sufficient to filter bacteria having dimensions less than about five microns from the airstream developed during the suctioning process. Other filter materials are known to remove bacteria and particulate matter from medical gases. For example, W. L. Gore and Associates, Inc., of Elkton, Md., makes filters known as GORE-TEX ® membranes and laminates to vent air while preventing fluid leakage or bacterial entry. Descriptions of these membranes and laminates are found in three W. L. Gore and Associates, Inc. publications, entitled, "GORE-TEX Membrane Products" (1980); "GORE-TEX Expanded PTFE" (1978); and "GORE-TEX Expanded PTFE" (an ICI Engineering Platics publication reprint, No. 4, 1975). U.S. Pat. No. 4,187,390 also describes some of these filter materials.

While body liquid control and particulate matter filration, including bacteria, have been addressed by the prior art in suction canister systems, there is still a need for a straightforward, easily fabricated system wherein both liquid overflow control and bacteria filtration can be handled by a single control element. In addition, it is also desirable that the mechanism for controlling liquid overflow also be capable of shutting down the vacuum system which draws liquid into the suction canister. It is to these ends that the present invention is directed.

SUMMARY OF THE INVENTION

The suction canister assembly of the present invention comprises an enclosed receptacle having a first opening for providing suction to the receptacle and a second opening for drawing fluids, including liquids and gases, into the receptacle during suction. A unitary shut-off valve/filter element is associated with the interior side of the first opening and is oriented within the receptacle to be contacted by liquid in the receptacle which rises therein. The valve/filter element is porous and is adpated to filter particulate matter from gas passing therethrough, and is capable of developing sufficiently high surface tension under liquid contact to serve as a barrier against liquid passage therethrough at pressure differentials across the element when vacuum is applied to one side of the element, with normal atmospheric pressure conditions on the opposite side. With such structure, the valve/filter element is adapted to terminate suction through the suction opening when liquid rises in the receptacle to completely cover the element.

In accordance with another embodiment of the present invention, the suction canister assembly comprises a cup-shaped receptacle having an open mouth portion. A cover is sealably connected to the receptacle over the mouth portion, with the cover having a suction opening therethrough adapted to communicate with a source of vacuum applied to the exterior side of the suction opening. A liquid passage opening extends through the cover and is adapted to communicate with a source of liquid exterior to the canister so that liquid is passable therethrough to enter the receptacle under suction conditions provided through the suction opening by the vacuum source. A unitary shut-off valve/filter element is connected to the interior side of the suction opening and is oriented within the receptacle to be contacted by liquid therein which rises to a pre-determined level. This valve/filter element is porous with a maximum pore rating of about 0.5 microns for filtering particulate matter including microorganisms. Furthermore, the valve/filter element is capable of developing sufficiently high surface tension under liquid contact to serve as a barrier against liquid passage therethrough at pressure differentials across the element up to 14.7 psi (1,032 g/cm$^2$).

In accordance with still another embodiment of the present invention, the unitary shut-off valve/filter element is a thin porous membrane adapted to filter particulate matter from gas passing therethrough, while capable of developing sufficiently high surface tension under liquid contact to serve as a barrier against liquid passage therethrough. The thin membrane is connected to a substantially rigid support interposed between the element and the suction opening on the cover of the assembly. Fluid channel means on the support communicate with the suction opening so that the element will be prevented from totally collapsing against the support during suction.

In still another embodiment of the present invention, the shut-off valve/filter element is laminated to a thin porous backing sheet adapted to provide strength and stability to the composite structure of valve/filter element and backing sheet. This composite structure is connected to the suction opening so that the element faces the interior of the receptacle so as to be first contacted by liquid rising therein.

In still another embodiment of the present invention, a valve/filter housing encloses the unitary shut-off valve/filter element. This housing includes an upper portion and a lower portion with the upper portion being connected to the interior side of the suction opening in the canister cover. The upper portion thus serves as a support interposed between the valve/filter element and the suction opening, and includes fluid channel means communicating with the suction opening so that the element will be prevented from totally collapsing against the upper portion during suction. A lower portion of the housing includes an open framework to protect the valve/filter element and to allow passage of gas and liquid therethrough to contact the element. Preferably, the valve/filter element is a thin porous membrane adapted to filter particulate matter from gas passing therethrough and also capable of developing sufficiently high surface tension under liquid contact to serve as a barrier against liquid passage therethrough. When mounted on the cover, the housing is oriented so that the valve/filter element within is contacted by liquid in the receptacle which rises to a pre-determined level.

In accordance with the principles of the present invention, the unitary shut-off valve/filter element combines two functions into one. It filters particulate matter, including bacteria, during the suction process and also seves as a shut-off valve to terminate suction through the suction opening when liquid rises in the receptacle to cover the element. In this invention, the valve/filter element not only controls liquid overflow in the canister, but serves to shut down the source of vacuum which is applied to the contents inside the canister. This is due to the sufficiently high surface tension which the valve/filter element is capable of developing whereby liquid is prevented from passing through the pores of this element. Thus, once liquid contacts this element and completely covers the open pores, the vacuum tending to pull the liquid through the element will not be strong enough to force the liquid therethrough. The valve/filter element materials which are selected to accomplish this feature will serve to prevent liquid from passing therethrough at pressure differentials normally encountered in the hospital environment, and even up to a full vacuum load which could be normally encountered at standard atmospheric pressure conditions. Other features of the various embodiments of the invention as mentioned above, will be pointed out in the ensuing detailed description.

DETAILED DESCRIPTION

Figure 1:
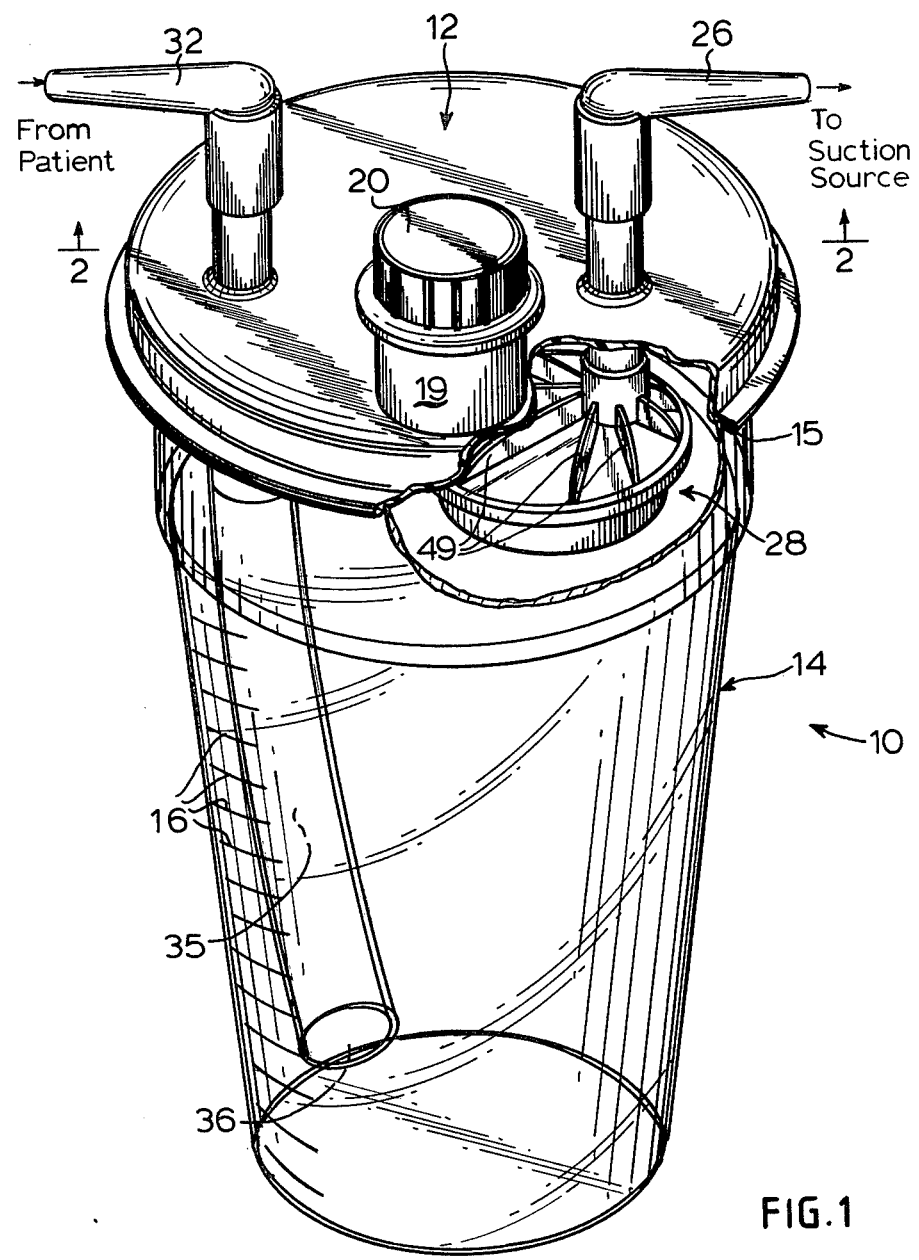
FIG. 1 is a perspective view of the preferred embodiment of the suction canister assembly of the present invention.

While this invention is satisfied by embodiments in many different forms, there is shown in the drawings and will herein be described in detail preferred embodiments of the invention, with the understanding that the present disclosure is to be considered as exemplary of the principles of the invention and is not intended to limit the invention to the embodiments illustrated. The scope of the invention will be measured by the appended claims and their equivalents.

Adverting to the drawings, and FIG. 1 in particular, there is illustrated a suction canister assembly 10. Suction canister assembly 10 preferably is composed of two major items: a cover assembly 12 and a receptacle 14. The receptacle is preferably made of clear, rigid plastic material, and is cup-shaped with an open mouth portion 15. A plurality of gradation marks 16 may be included around the periphery of the cylindrically-shaped receptacle in order to provide the user with an indication of volume of liquid collected. Typical suction canisters may hold a volume of 1,000–1,500 cubic centimeters. However, these volumes may vary according to choice and depending upon the intended use of the suction canister.

Figure 2:
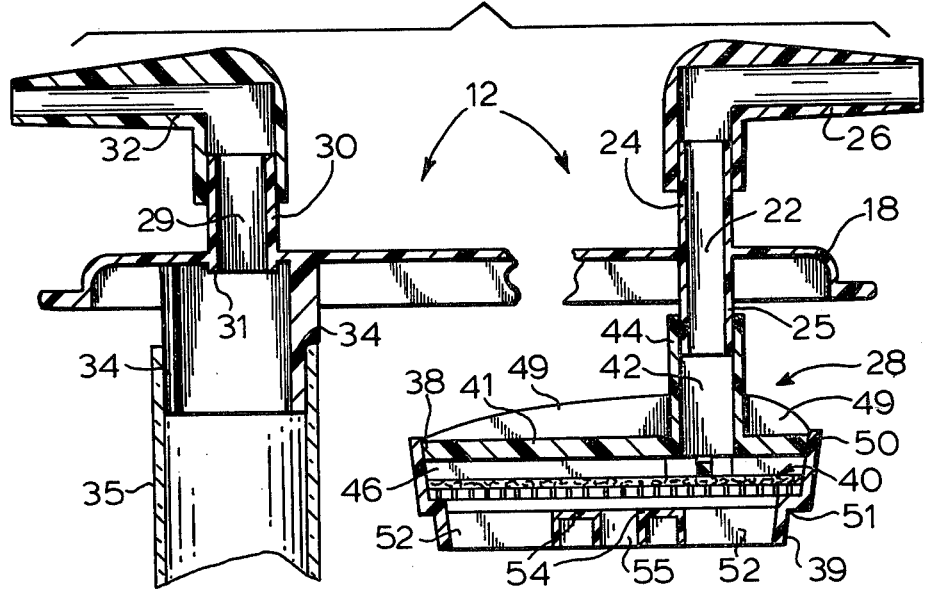
FIG. 2 is a cross-sectional view of the cover assembly of FIG. 1 taken along line 2—2 thereof.

Cover assembly 12 is more clearly illustrated in FIG. 2, taken in conjunction with FIG. 1. As can be seen in these drawings, cover assembly 12 includes a cover 18 which is preferably circularly-shaped and is intended to sealably fit over mouth portion 15 of receptacle 14. The fit between cover 18 and receptacle 14 should be sufficiently airtight so that a vacuum can be applied to the inside of the receptacle without leakage around the rim of mouth portion 15 where it contacts cover 18. A sufficiently tight snap-fit not only allows assembly of the cover assembly to the receptacle, but also is generally adequate for sealing the receptacle during vacuum conditions. Cover 18 may include a pour spout 19 with a removable lid 20 covering same. This, of course, will allow liquid inside the receptacle to be poured therefrom, if desired.

A suction opening 22 extends through cover 18 defined by an upper post 24 on the exterior side of the cover and a lower post 25 on the interior side of the cover. A hollow elbow connector 26 is connected to post 24. A tube or other flexible line (not shown) extends between connector 26 and a suction source, such as a pump, in order to provide a source of vacuum through suction opening 22. Connected to post 25 on the interior side of cover 18 is a valve/filter housing 28, illustrated in FIGS. 1 and 2 in its preferable form, the details of which will be discussed hereinbelow.

Cover 18 also includes a liquid passage opening 29 therethrough, defined by an upper post 30 on the exterior side of the cover and a short lower post 31 on the interior side of the cover. Connected to upper post 30 is a hollow connector 32 similar in all respects to connector 26 hereinbefore described. A tube or flexible line (not shown) is connected to connector 32 and extends to a source of body liquid, such as found in a patient undergoing a surgical operation. Surrounding short lower post 31 on the interior side of cover 18 is a longer lower post 34. Connected to longer lower post 34 and extending downwardly is a flexible sheath 35, preferably transparent. This sheath depends deep into receptacle 14 and includes an opening 36 at its distal end. As liquid from the body source passes through liquid passage 29 it is funneled through sheath 35 directly toward the bottom of the receptacle. Therefore, sheath 35 serves as a splash guard or the like in order to prevent body liquids from splashing directly against the valve/filter housing. This sheath is merely a preferred feature and is not essential to the operation of the canister assembly. In essence, once the vacuum source is connected to connector 26, a negative pressure gradient is communicated to the inside of receptacle 14. This suction, in turn, draws liquid from the source in the patient through liquid passage opening 29 for collection of this liquid inside the receptacle. These features of a suction canister system, in general, are well known.

Figure 3:
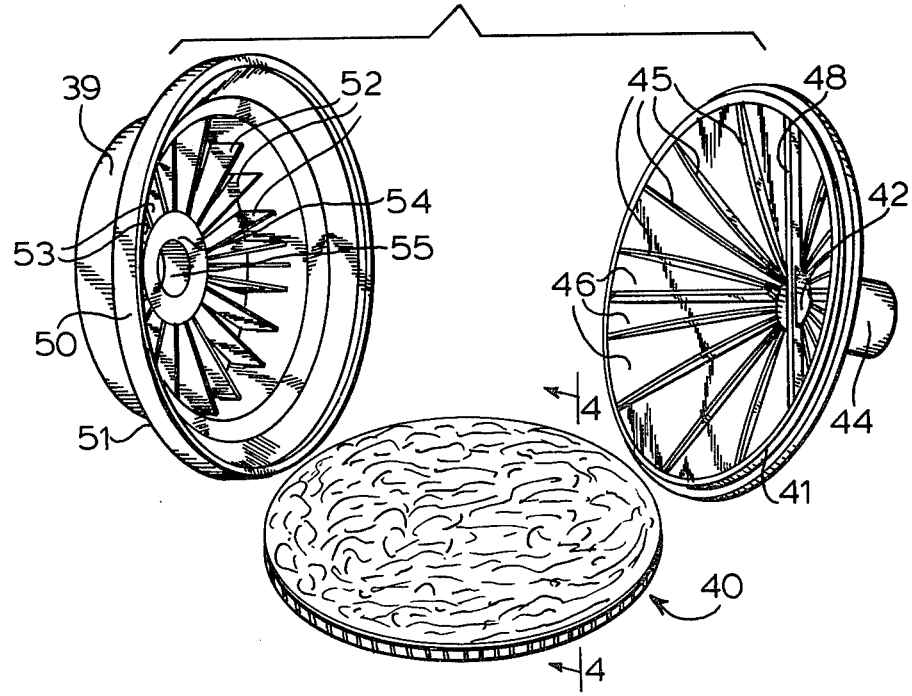
FIG. 3 is an exploded perspective view of the components of the valve/filter housing assembly of FIG. 1.
Figure 4:
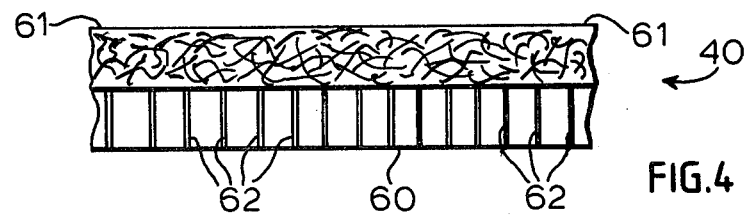
FIG. 4 is an enlarged cross-sectional view of the filter element and backing sheet taken along line 4—4 of FIG. 3.
Figure 5:
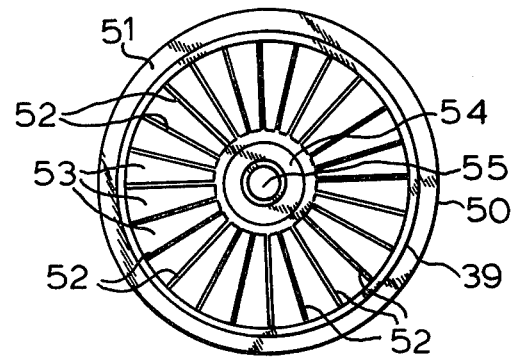
FIG. 5 is a bottom plan view of the valve/filter housing of FIG. 1.

Turning now to FIGS. 3, 4 and 5, taken together with FIGS. 1 and 2, the details of preferred valve/filter housing 28 are illustrated. Housing 28 includes an upper portion 38 and a lower portion 39, both enclosing the preferred composite valve/filter assembly 40 within. Referring to upper portion 38, it includes a generally planar surface 41 preferably circularly-shaped. A hole 42 extends through the planar surface, and is defined by an upwardly extending post 44. This post is connected to lower post 25 on the interior side of cover 18 so that the inside of housing 28 is in fluid communication with suction opening 22. Both hole 42 and upwardly extending post 44 are offset from the center of upper portion 38 to allow the housing to be connected to post 25 without interfering with the wall of receptacle 14. This is due to the fact that suction opening 22 extends through cover 18 toward the outside periphery thereof.

On the under or interior side of the planar surface 41 is a plurality of ribs 45, spaced from each other and preferably extending radially from hole 42 and terminating at the outside rim of the planar surface. Between adjacent ribs 45 are channels 46, each channel being in fluid communication with hole 42. One rib 48 extends across hole 42 to provide support to the valve/filter structure as hereinafter described. On the outside surface of upper portion 38 is a plurality of structural stiffeners 49 which provide additional transverse rigidity to the upper portion.

Referring now to lower portion 39, it is substantially cylindrically-shaped including a cup portion 50 defined by a shoulder 51. As can be seen particularly in FIG. 2, both composite valve/filter structure 40 and planar surface 41 of the upper portion are sized to fit within cup portion 50 to rest on shoulder 51. It is preferable that the upper and lower portions of housing 28 be sealed together such as by heat sealing (if thermoplastic materials are used), adhesives, mechanical wedging or the like. The bottom surface of lower portion 39 is defined by a plurality of spaced, radially directed spokes 52, with a space 53 between adjacent spokes. These spokes provide transverse rigidity to the bottom surface of the lower portion. The spokes are connected at their interior ends to a hub 54 which includes an opening 55 therethrough to provide sufficient open space within this framework for allowing liquids and gases to enter the housing. It is also noted that the spoked, bottom surface of the lower portion is preferably spaced a short distance from the valve/filter structure; this spacing and the spoke structure of the lower portion contribute to uniformly distribute any organisms or aerosols which may be present during suction over the entire surface of the valve/filter element structure. This uniform distribution enables the valve/filter element to function more effectively over longer periods of time. Furthermore, the spokes also prevent damage to the valve/filter element inside especially during handling, shipment and usage, due to the transverse rigidity which they impart.

When composite valve/filter structure 40 is placed between upper portion 38 and lower portion 39 of the housing, it overlies ribs 45 on the upper portion. During suction, the pressure gradient tends to draw the valve/filter element upwardly; ribs 45 then serve to prevent the valve/filter element from totally collapsing against planar surface 41, whereas rib 48 serves to prevent the valve/filter element from being sucked into hole 42. As a result of this structure, all gases which pass through valve/filter element enter channels 46 which communicate with hole 42. Therefore, the support provided by the rib structure provides adequate gas passage through the valve/filter element during the suction procedure. Before turning to the details of the valve/filter element, FIGS. 1 and 2 illustrate the preferred orientation of the valve/filter housing, and particularly the valve/filter element within. In this embodiment, the valve/filter element is oriented to be substantially parallel to the free upper surface of liquid which enters the receptacle; in this configuration, composite valve/filter element 40 is thus in a substantially horizontal position. The function of this embodiment will be described more fully hereinafter in conjunction with FIG. 6.

Referring now more specifically to FIGS. 3 and 4, the preferred composite valve/filter element 40 is illustrated. Composite structure 40 includes a valve/filter element 60, and in preferable embodiments of the present invention, a thin porous backing sheet 61 laminated to element 60. Valve/filter elment 60 is preferably a thin porous membrane which includes a plurality of pores 62 therethrough illustrated in FIG. 4 in graphic form. It is appreciated that those skilled in the art will recognize that pores 62 may not extend straight through the thickness of the valve/filter element material; in this regard, the valve/filter element material has a pore rating rather than merely characterizing same by pore size. In the preferred form, the pore rating of the valve/filter element is about 0.5 microns or perhaps as low as 0.45 microns. This pore rating should be sufficient to entrap microorganisms which may be found in a hospital environment in which the present invention is intended to be used. In addition to this preferable pore rating, the valve/filter element desirably prevents liquid from passing therethrough even with substantially high pressure differentials across the element. In particular, valve/filter element 60 should be capable of developing sufficiently high surface tension under liquid contact to seve as a barrier against liquid passage therethrough at pressure differentials across the element up to 14.7 psi (1,032 g/cm$^2$). In other words, even at a pressure differential of 14.7 psi across the valve/filter element, no liquid will be permitted to pass therethrough. Inasmuch as the standard atmospheric pressure condition is about 14.7 psi, this valve/filter element should be capable of withstanding full vacuum conditions thereacross under standard atmospheric pressure levels. However, most hospital suction generating sources only apply a pressure gradient of about 5 psi (210 g/cm$^2$). Therefore, there normally would be a considerable margin of safety whereby liquid will be prevented from passing through the valve/filter element under the types of pressure gradient generated by typical hospital suction devices. On the other hand, the valve/filter element can be chosen to withstand a pressure gradient as high as 21 psi (1,550 g/cm$^2$).

Although valve/filter element 60 may be self-sustaining for suction canister applications if its thickness is at least 0.006 inches (0.015 cm), it is preferable to maintain the valve/filter element in a thin membrane state, while providing additional backing strength by employment of backing sheet 61. In this respect, although many material thicknesses fall within the purview of this invention, it is possible to fabricate a composite thickness of both valve/filter element and backing sheet of between 0.006 and 0.015 inches (0.015 and 0.038 cm). Even though the composite structure is very thin, backing sheet 61 will provide sufficient structural integrity and stability to the structure to prevent the valve/filter element from being torn apart or otherwise becoming abused. Some nonwoven fabrics are suitable for this backing sheet inasmuch as they are porous and can be made very thin, while strong. In this respect, and although other materials may be chosen, such nonwoven material may be selected from the group of materials consisting of polypropylene, polyethylene and polyester. On the other hand, suitable materials for the valve/filter element, satisfying the above-noted criteria, are polymeric materials selected from polytetrafluoroethylene, polyester, polyvinylchloride, polypropylene, polyethylene and the like, preferably ranging in thickness of from about 0.003 to 0.010 inches (0.0076 and 0.0025 cm). Such laminated composite structures of valve/filter element and backing sheet as just described are available from W. L. Gore and Associates, Inc., of Elkton, Md., and are sold as GORE-TEX membrane products (as heretofore mentioned). The preferred valve/filter element is polytetrafluoroethylene, whereas the preferred backing sheet is a nonwoven polypropylene. The composite thickness of preferred valve/filter element and backing sheet is approximately 0.008 inches (0.020 cm). A preferred pore rating is 0.5 microns, with the valve/filter element capable of withstanding a pressure differential across of up to 21 psi (1,550 g/cm$^2$) before any liquid will pass therethrough. However, gases will readily pass through this valve/filter element, but the pore rating should prevent most bacteria from passing through this element. Also, the preferred valve/filter element of the present invention, such as the aforementioned GORE-TEX material, desirably prevents aerosol particles or droplets from passing therethrough. Accordingly, for purposes of the present invention, when reference is made to the prevention of liquid through the valve/filter element, it also includes the prevention of aerosol particles or droplets therethrough. This is due to the fact that aerosol droplets usually have a size ranging between 0.5 and 50 microns. With the pore rating of the valve/filter element being at the minimum end of the aerosol particle size, these aerosol particles or droplets should be prevented from passing through the valve/filter element of the present invention.

During assembly of the valve/filter element into housing 28, it is preferable to place composite structure 40 so that valve/filter element 60 faces downwardly or toward lower portion 39. In this way, liquid entering into housing through spaces 53 and hole 55 in the lower portion of the housing will contact valve/filter element 60 first. Since it is this surface that develops the high surface tension under liquid contact, liquid contacting the surface will be prevented from passing through. It should also be pointed out that if composite structure 40 is handled properly, it could be used in the housing assembly without lower portion 39 attached. Although not specifically shown in the drawings, composite valve/filter structure 40 could be secured directly to upper portion 38, serving as a support member, with valve/filter element 60 facing downwardly. Thus, any liquid inside the canister which rises will directly contact valve/filter element 60 if the lower portion of the housing has not been employed.

Although many materials may be selected for the various components of the present invention, since the suction canister assembly is intended to be disposable, rigid plastic materials are preferably used. While sizes and shapes of the various components may vary according to design or choice, a typical valve/filter element in the present invention is circularly-shaped and has a flow area for filtration purposes of approximately 3 square inches (19.4 cm$^2$). Also, of the total surface area of the valve/filter element, between 50% and 90% of the total surface area may include pores.

Figure 6:
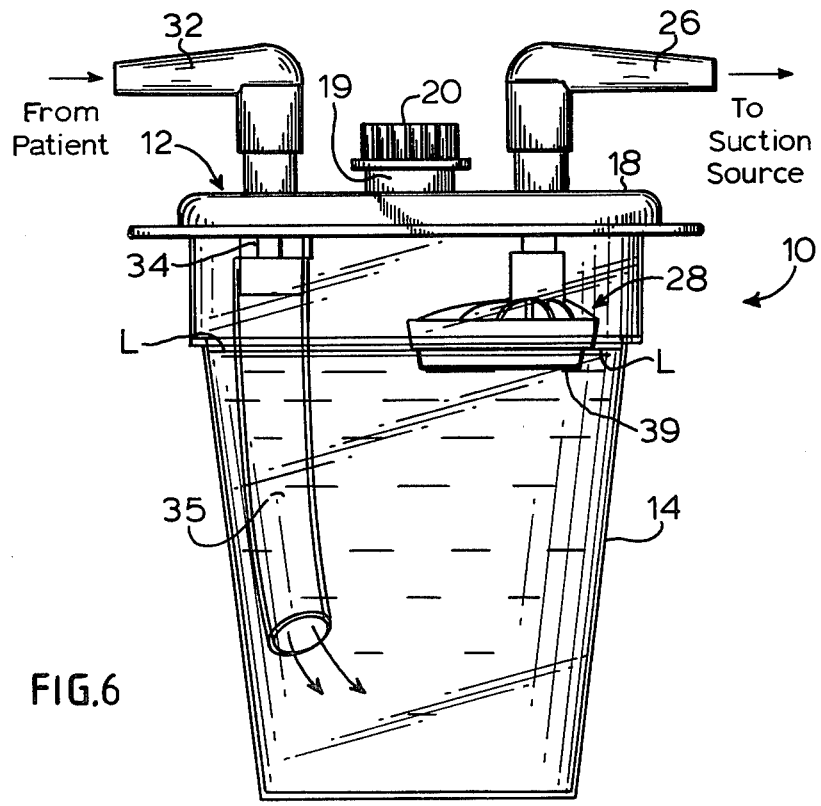
FIG. 6 is a side elevational view of the suction canister assembly of FIG. 1 illustrated with liquid therein rising to a level which would cause suction termination.

FIG. 6 depicts the preferred suction canister assembly of the present invention in use. Suchtion is applied through connector 26 and into receptacle 14 through valve/filter housing 28. The porous nature of the valve/filter element (inside housing 28) allows the suction forces to be transmitted through the valve/filter housing so that a negative pressure gradient is applied inside receptacle 14. As a result, liquid from the patient is drawn through connector 32 and through sheath 35 so that it is collected inside the receptacle. As long as the suction is applied and the level of liquid inside the receptacle remains low, the negative pressure gradient remains, thereby pulling more liquid into the receptacle. During this suction process while liquid is filling the receptacle, air and other gases, already in the receptacle or entering through sheath 35, are filtered when they pass through the valve/filter element hereinabove described. Accordingly, particulate matter, including bacteria, traveling from the patient into the receptacle is filtered and collected on the valve/filter element. Therefore, contamination of the vacuum pump (which is not a disposable item) and the environment surrounding the vacuum pump is also prevented. Once the liquid level L inside the receptacle reaches a certain height, it passes through the open framework construction of lower portion 39 of the valve/filter housing. As soon as the liquid completely contacts the valve/filter element within, no liquid will pass through the element. Moreover, the liquid contacting the valve/filter element will also close off the vacuum which had been applied to the inside of the receptacle. In this regard, no further liquid can be drawn into the receptacle since the valving aspects of the valve/filter element effectively close off the negative pressure gradient which had been applied. Once this occurs, the attendant disconnects the suction canister assembly from the suction source and from the tubing to the patient.

Figure 7:
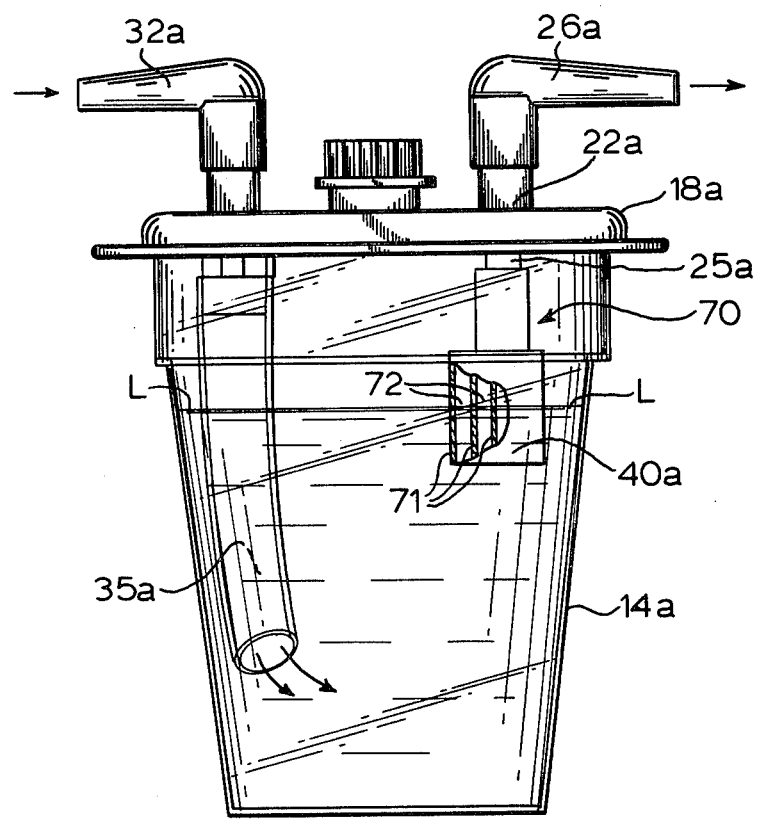
FIG. 7 is a side elevational view of a suction canister assembly with an alternative valve/filter housing shown partially in cross-section to view the internal components thereof.

Although many embodiments fall within the purview of the present invention, one alternative embodiment is illustrated in FIG. 7. All of the components of this suction canister assembly are similar to those components described above and are designated with corresponding numerals followed by suffix "a." However, a different valve/housing assembly 70 is employed in the embodiment of FIG. 7. Instead of the horizontal arrangement of the filter element as previously described, valve/filter housing 70 is connected to suction opening 22a through post 25a in a vertical orientation. In this embodiment, housing 70 includes an open frame, drum-like structure, characterized by vertically extending spaced bars 71, with spaces 72 between adjacent bars. Wrapped around the periphery defined by bars 71 is a valve/filter element, such as the preferred valve/filter composite structure 40a. In this orientation, the valve/filter element is oriented to be substantially perpendicular to the free upper surface of liquid which enters the receptacle. During use, while liquid is filling the receptacle, air and other gases pass through valve/filter element 40a and travel through spaces 72 and suction opening 22a while the suction is operating. Particulate matter is filtered so that the air and gases are relatively free from particulate matter, including bacteria, when the suction pump is operating. When the liquid rises in the receptacle, it is noted that the complete valve/filter element will not be completely contacted at the same liquid level, due to the vertical orientation of the element. Therefore, the attendant operating the suction pump and observing the suction canister assembly should be able to notice a slowing down of the liquid collection inside the receptacle. As more and more surface area is contacted by rising liquid in the receptacle, the suction will become more tedious as the rate of liquid collection declines. In this regard, once the attendant notices the slowed rate of liquid collection, the canister assembly can be disconnected and replaced with an empty canister assembly. On the other hand, the attendant can wait until liquid completely covers the valve/filter element whereupon the vacuum will be completely shut down. This embodiment of FIG. 7 therefore provides the attendant with an indication that the canister assembly is nearly full as soon as the attendant perceives the slow down of liquid collection.

Thus, it can be seen that the present invention provides a suction canister assembly with a unique, combined valve and filter feature. The filter not only filters out particulate matter, but preferably also filters bacteria from air or gases passing through the suction canister assembly. On the other hand, liquid contact of this element serves as a valve to not only control liquid overflow in the canister assembly, but also to close off suction into the canister assembly so that no more liquid can be collected therein.

What is claimed is:

1. A suction canister assembly for collecting body fluids comprising:
    a cup-shaped receptacle having an open mouth portion and an opposed bottom wall;
    a cover sealably connected to said receptacle over said mouth portion, said cover having a suction opening therethrough adapted to communicate with a source of vacuum applied to the exterior side of said suction opening, and having a liquid passage opening means therethrough adapted to communicate with a source of liquid exterior to said canister so that liquid is passable therethrough to enter said receptacle under suction conditions provided through said suction opening by said vacuum source; and
    a unitary shut-off valve/filter element connected to the interior side of said suction opening lying within a single suction path extending only from the interior of said receptacle to said suction opening so that all gases are exchanged between said receptacle and said suction opening through said element, said element adapted to lie substantially parallel to the free upper surface of liquid which enters said receptacle when said bottom wall rests on a substantially horizontal surface, said element oriented within said receptacle to be contacted by liquid in said receptacle which rises to a predetermined level, said element being porous with a maximum pore rating of about 0.5 micron for filtering particulate matter including microorganisms from gas passing therethrough, said element capable of developing sufficiently high surface tension under liquid contact to serve as a barrier against liquid passage therethrough at pressure differentials across said element up to 14.7 psi, said element adapted to terminate suction through said suction opening at suction pressures up to 14.7 psi when liquid rises in said receptacle to completely cover said element.

2. The assembly of claim 1 wherein said element is a thin membrane.

3. The assembly of claim 2 wherein said membrane has a thickness of between 0.003 and 0.010 inches.

4. The assembly of claim 3 wherein said membrane has a porosity of between 50% and 90% of total surface area of said membrane.

5. The suction canister assembly of claim 1 wherein said filter element is laminated to a thin porous backing sheet adapted to provide stability to the composite structure of said element and said sheet, said composite structure connected to said suction opening so that said element faces the interior of said receptacle so as to be contacted by liquid therein.

6. The assembly of claim 5 wherein said element and said backing sheets are thin membrane.

7. The assembly of claim 6 wherein said composite structure has a thickness between 0.006 and 0.015 inches.

8. The assembly of claim 6 wherein said backing sheet membrane is made of nonwoven material.

9. The assembly of claim 8 wherein said nonwoven material is selected from the group of materials consisting of polyester, polyethylene and polypropylene.

10. A suction canister assembly for collecting body fluids comprising:
    a cup-shaped receptacle having an open mouth portion and an opposed bottom wall;
    a cover sealably connected to said receptacle over said mouth portion, said cover having a suction opening therethrough adapted to communicate with a source of vacuum applied to the exterior side of said suction opening, and having a liquid passage opening means therethrough adapted to communicate with a source of liquid exterior of said canister so that liquid is passable therethrough to enter said receptacle under suction conditions provided through said suction opening by said vacuum source; and
    a unitary shut-off valve/filter element connected to the interior side of said suction opening lying within a single suction path extending only from the interior of said receptacle to said suction opening so that all gases are exchanged between said receptacle and said suction opening through said element, said element adapted to lie substantially parallel to free upper surface of liquid which enters said receptacle when said bottom wall rests on a substantially horizontal surface, said element oriented within said receptacle to be contacted by liquid in said receptacle which rises to a predetermined level, said element being a thin porous membrane adapted to filter particulate matter from gas passing therethrough, said element capable of developing sufficiently high surface tension under liquid contact to serve as a barrier against liquid passage therethrough when vacuum is applied to the side of said element facing said suction opening at normal atmospheric pressure conditions, said thin membrane connected to a substantially rigid support interposed between said element and said suction opening, said support including fluid channel means communicating with said suction opening so that said element will be prevented from totally collapsing against said support during suction, said element adapted to terminate suction through said suction opening when liquid rises in said receptacle to completely cover said element.

11. The assembly of claim 10 wherein said support is generally planar with a hole extending therethrough, said support being connected to said cover so that said hole in the support and the suction opening are in fluid communication, said element being connected to a first planar surface of said support.

12. The assembly of claim 11 wherein said channel means is defined by a plurality of spaced ribs on said first surface with said element overlying said ribs and a channel being recessed between adjacent ribs so that gas can freely pass through said element and into said channels for communication with said suction opening.

13. The assembly of claim 12 wherein said ribs extend radially from said hole with said channels converging on and being in fluid communication with said hole.

14. The assembly of claim 12 wherein said support includes a plurality of structural stiffeners on the opposite planar surface to provide additional transverse rigidity to said support.

15. A suction canister assembly comprising:
a cup-shaped receptacle having an open mouth portion;
a cover sealably connected to said receptacle over said mouth portion, said cover having a suction opening therethrough adapted to communicate with a source of vacuum applied to the exterior side of said suction opening, and having a liquid passage opening therethrough adapted to communicate with a source of liquid exterior to said canister so that liquid is passable therethrough to enter said receptacle under suction conditions provided through said suction opening by said vacuum source; and
a unitary shut-off valve/filter element connected to the interior side of said suction opening and oriented within said receptacle to be contacted by liquid in said receptacle which rises to a predetermined level, said element being a thin porous membrane adapted to filter particulate matter from gas passing therethrough, said element capable of developing sufficiently high surface tension under liquid contact to serve as a barrier against liquid passage therethrough when vacuum is applied to the side of said element facing said suction opening at normal atmospheric pressure conditions, said element adapted to terminate suction through said suction opening when liquid rises in said receptacle to completely cover said element, said thin membrane connected to a substantially rigid support interposed between said element and said suction opening, said support being generally planar with a hole extending therethrough and being connected to said cover so that said hole in the support and the suction opening are in fluid communication, said element being connected to a first planar surface of said support, said support including fluid channel means defined by a plurality of spaced ribs on said first surface with said element overlying said ribs and a channel being recessed between adjacent ribs so that gas can freely pass through said element and into said channels for communication with said suction opening, said ribs extending radially from said hole with said channels converging on and being in fluid communication with said hole wherein at least one rib extends across said hole so that said element is prevented from collapsing into said hole during suction.

16. A suction canister assembly for collecting body fluids comprising:
an enclosed receptacle having a first opening for providing suction to said receptacle, a second opening for drawing fluids, including liquids or gases, into said receptacle during suction and a bottom wall opposed from said first opening; and
a unitary shut-off valve/filter element connected to the interior side of said first opening lying within a single suction path extending only from the interior of said receptacle to said first opening so that all gases are exchanged between said receptacle and said first opening through said element, said element adapted to lie substantially parallel to the free upper surface of liquid which enters said receptacle when said bottom wall rests on a substantially horizontal surface, said element oriented within said receptacle to be contacted by liquid in said receptacle which rises to a predetermined level within a receptacle, said element being porous with a maximum pore rating of about 0.5 micron for filtering particulate matter including microorganisms from gas passing therethrough, said element capable of developing sufficiently high surface tension under liquid contact to serve as a barrier against liquid passage therethrough at pressure differentials across said element up to 14.7 psi, said element adapted to terminate suction through said first opening suction pressures up to 14.7 psi when liquid rises in said receptacle to completely cover said element.

17. A suction canister assembly for collecting body fluids comprising:
a cup-shaped receptacle having an open mouth portion and an opposed bottom wall;
a cover sealably connected to said receptacle over said mouth portion, said cover having a suction opening therethrough adapted to communicate with a source of vacuum applied to the exterior side of said suction opening, and having a liquid passage means opening therethrough adapted to communicate with a source of liquid exterior to said canister so that liquid is passable therethrough to enter said receptacle under suction conditions provided through said suction opening by said vacuum source; and
a valve/filter housing enclosing a unitary shut-off valve/filter element within and including an upper portion and a lower portion, said upper portion being connected to the interior side of said suction opening and serving as a support interposed between said element and said suction opening and including fluid channel means communicating with said suction opening so that said element is prevented from totally collapsing against said upper portion during suction, said element lying within a single suction path extending only from the interior of said receptacle to said suction opening so that all gases are exchanged between said receptacle and said suction opening through said element, said lower portion including an open framework to protect said element and to allow passage of gas an liquid therethrough to contact said element, said element being a thin porous membrane adapted to filter particulate matter from gas passing therethrough, said element capable of developing sufficiently high surface tension under liquid contact to serve as a barrier against liquid passage therethrough when vacuum is applied to the side of said element facing said suction opening at normal atmospheric pressure conditions, said housing oriented so that said element is contacted by liquid in said receptacle which rises to a predetermined level, said element adapted to lie substantially parallel to the free upper surface of liquid which enters said receptacle when said bottom wall rests on a substantially horizontal surface, said element adapted to terminate suction through said suction opening when liquid rises in said receptacle to completely cover said element.

18. The assembly of claim 17 wherein said upper portion is generally planar with a hole extending therethrough in fluid communication with said suction opening, said element being connected to said housing between said upper and lower portions.

19. The assembly of claim 18 wherein said channel means is defined by a plurality of spaced ribs on the inside surface of said upper portion with a channel being recessed between adjacent ribs, said element overlying said ribs so that gas can freely pass through said element and into said channels for communication with said suction opening.

20. The assembly of claim 19 wherein said upper portion includes a plurality of structural stiffeners on the outside surface thereof to provide additional transverse rigidity to said upper portion.

21. The assembly of claims 17 or 20 wherein said lower portion includes a bottom surface spaced a short distance from said element, said bottom surface including a plurality of spaced, radially directed spokes to provide transverse rigidity to said bottom surface.

22. The assembly of claim 21 wherein said housing is circular in cross-section with said element lying across said circular cross-section.

23. The assembly of claims 10 or 17 which further includes a thin porous backing sheet laminated to said element to provide stability to the composite structure of said element and said sheet, said composite structure connected to said support so that said element faces the interior of said receptacle so as to be contacted by liquid therein.

24. The assembly of claims 1, 5, 10, 16 or 17 wherein said element is made of polymeric material.

25. The assembly of claim 24 wherein said polymeric material is selected from the group consisting of polytetrafluoroethylene, polyester, polyvinylchloride, polypropylene and polyethylene.

26. The assembly of claims 10 or 17 wherein said element has a maximum pore rating of about 0.5 micron and serves as a substantial barrier to particles about 0.5 micron and larger, said element also serving as a liquid barrier at pressure differentials across said element up to 14.7 psi.

27. A suction canister assembly comprising:
a cup-shaped receptacle having an open mouth portion;
a cover sealably connected to said receptacle over said mouth portion, said cover having a suction opening therethrough adapted to communicate with a source of vacuum applied to the exterior side of said suction opening, and having a liquid passage opening therethrough adapted to communicate with a source of liquid exterior to said canister so that liquid is passable therethrough to enter said receptacle under suction conditions provided through said suction opening by said vacuum source; and
a valve/filter housing enclosing a unitary shut-off valve/filter element within and including an upper portion and a lower portion, said upper portion being connected to the interior side of said suction opening and serving as a support interposed between said element and said suction opening, said upper portion being generally planar with a hole extending therethrough in fluid communication with said suction opening and including fluid channel means defined by a plurality of spaced ribs on the inside surface of said upper portion with a channel being recessed between adjacent ribs, said element overlying said ribs so that gas can freely pass through said element and into said channels for communication with said suction opening, wherein at least one rib extends across said hole so that said element is prevented from collapsing into said hole during suction, said lower portion including an open framework to protect said element and to allow passage of gas and liquid therethrough to contact said element, said element being a thin porous membrane adapted to filter particulate matter from gas passing therethrough, said element capable of developing sufficiently high surface tension under liquid contact to serve as a barrier against liquid passage therethrough when vacuum is applied to the side of said element facing said suction opening at normal atmospheric pressure conditions, said housing oriented so that said element is contacted by liquid in said receptacle which rises to a predetermined level, said element adapted to terminate suction through said suction opening when liquid rises in said receptacle to completely cover said element.

* * * * *

UNITED STATES PATENT AND TRADEMARK OFFICE
CERTIFICATE OF CORRECTION

PATENT NO. : 4,465,485

DATED : August 14, 1984

INVENTOR(S) : James S. Kashmer, John K. Klimbach and Randall P. Vandetti

It is certified that error appears in the above-identified patent and that said Letters Patent are hereby corrected as shown below:

Column 6, line 57, delete "seve" and substitute --serve-- in its place.

Column 12, line 39, Claim 16, delete "a" second occurrence, and substitute --said-- in its place.

Column 12, line 49, Claim 16, after "opening" add --at--.

Column 13, line 14, Claim 17, delete "an" and substitute --and-- in its place.

Signed and Sealed this

Twenty-sixth Day of February 1985

[SEAL]

Attest:

DONALD J. QUIGG

Attesting Officer     Acting Commissioner of Patents and Trademarks